(12) United States Patent
Steinert

(10) Patent No.: US 9,945,766 B2
(45) Date of Patent: Apr. 17, 2018

(54) DEVICE AND METHOD FOR MEASURING ENGINE FLOW AND MONITORING AIR FILTER PERFORMANCE

(71) Applicant: Bell Helicopter Textron Inc., Forth Worth, TX (US)

(72) Inventor: Alan H. Steinert, Fort Worth, TX (US)

(73) Assignee: Bell Helicopter Textron Inc., Fort Worth, TX (US)

(*) Notice: Subject to any disclaimer, the term of this patent is extended or adjusted under 35 U.S.C. 154(b) by 213 days.

(21) Appl. No.: 14/844,846

(22) Filed: Sep. 3, 2015

(65) Prior Publication Data

US 2017/0067769 A1    Mar. 9, 2017

(51) Int. Cl.

| G01M 15/00 | (2006.01) |
|---|---|
| G01N 11/02 | (2006.01) |
| B64C 27/12 | (2006.01) |
| B60L 1/00 | (2006.01) |
| F02D 41/22 | (2006.01) |
| F02M 35/10 | (2006.01) |
| F02D 41/18 | (2006.01) |
| F02M 35/09 | (2006.01) |
| F02D 41/14 | (2006.01) |

(52) U.S. Cl.
CPC .............. G01N 11/02 (2013.01); B60L 1/00 (2013.01); B64C 27/12 (2013.01); F02D 41/22 (2013.01); *F02D 41/18* (2013.01); *F02D 2041/1412* (2013.01); *F02D 2200/0402* (2013.01); *F02M 35/09* (2013.01); *F02M 35/10373* (2013.01); *Y02T 10/40* (2013.01)

(58) Field of Classification Search
USPC .............. 73/114.13, 114.14, 114.15, 114.31, 73/114.32, 114.33
See application file for complete search history.

(56) References Cited

U.S. PATENT DOCUMENTS

| 2003/0221480 | A1* | 12/2003 | Aschner | ................. F02M 35/09 73/114.34 |
|---|---|---|---|---|
| 2008/0190177 | A1* | 8/2008 | Wiggins | ................. F02M 35/09 73/49.7 |
| 2015/0344141 | A1* | 12/2015 | Brand | ................... B64D 33/02 95/273 |
| 2017/0067814 | A1* | 3/2017 | Steinert | .............. G01N 15/0826 |

OTHER PUBLICATIONS

Office Action in U.S. Appl. No. 14/844,865, dated Aug. 17, 2017, 12 pages.

* cited by examiner

*Primary Examiner* — Eric S McCall

(57) ABSTRACT

In one example embodiment, an engine flow measurement device features an engine data repository, one or more sensor units, and a measurement unit. The measurement system is configured to identify, from performance data, a maneuver performed during operation of the aircraft and to measure, for the identified maneuver, a plurality of maneuver flow values achieved during performance of the maneuver. The plurality of maneuver flow values correspond to a plurality of maneuver engine power values. Each of the plurality of maneuver flow values represent a volume of air flow through the air filter at a particular moment during performance of the maneuver.

20 Claims, 6 Drawing Sheets

| TIME | ENGINE POWER | ΔP |
|---|---|---|
| 1 | $RPM_1$ | $\Delta P_1$ |
| 2 | $RPM_2$ | $\Delta P_2$ |
| 3 | $RPM_3$ | $\Delta P_3$ |
| 4 | $RPM_4$ | $\Delta P_4$ |
| 5 | $RPM_5$ | $\Delta P_5$ |
| 6 | $RPM_6$ | $\Delta P_6$ |
| 7 | $RPM_7$ | $\Delta P_7$ |
| ⋮ | ⋮ | ⋮ |
|  | $RPM_{MAX\_M}$ | $\Delta P_{MAX\_M}$ |
| ⋮ | ⋮ | ⋮ |
| N-1 | $RPM_{N-1}$ | $\Delta P_{N-1}$ |
| N | $RPM_N$ | $\Delta P_N$ |

{ MAX ENGINE POWER ENTRY

FIG. 5

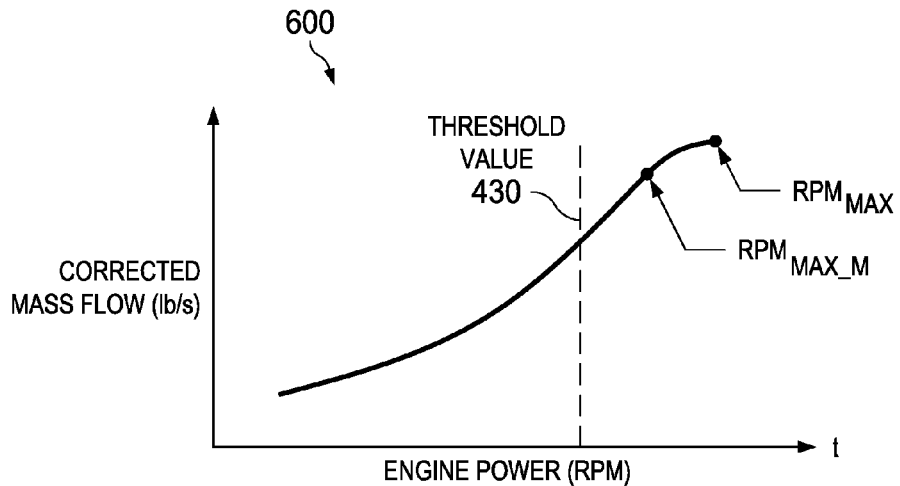
FIG. 6
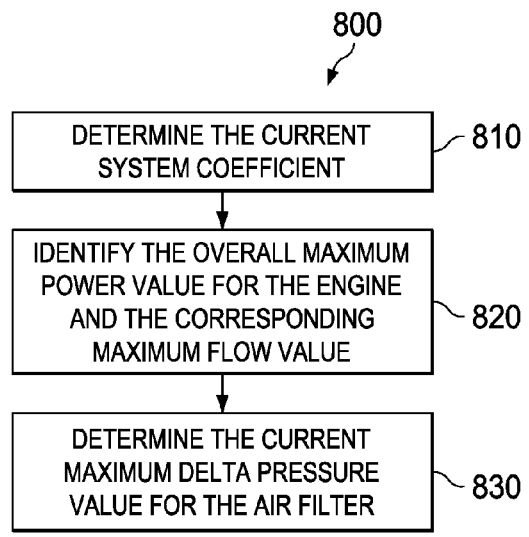
FIG. 8
| ENGINE POWER | MASS FLOW |
|---|---|
| $RPM_1$ | $Q_1$ |
| $RPM_2$ | $Q_2$ |
| $RPM_3$ | $Q_3$ |
| $RPM_4$ | $Q_4$ |
| $RPM_5$ | $Q_5$ |
| $RPM_6$ | $Q_6$ |
| $RPM_7$ | $Q_7$ |
| ⋮ | ⋮ |
| $RPM_{N-1}$ | $Q_{N-1}$ |
| $RPM_N$ | $Q_N$ |
FIG. 7

DEVICE AND METHOD FOR MEASURING ENGINE FLOW AND MONITORING AIR FILTER PERFORMANCE

GOVERNMENT RIGHTS

At least some of the subject matter of this application may have been made with government support under contract number N00019-12-G-0006 and delivery order number 0054. The government may have certain rights in the invention.

TECHNICAL FIELD

This invention relates generally to aircraft health, and more particularly, to an engine flow measurement device.

BACKGROUND

One example of an aircraft is a rotorcraft. A rotorcraft may include one or more rotor systems. One example of a rotorcraft rotor system is a main rotor system. A main rotor system may generate aerodynamic lift to support the weight of the rotorcraft in flight and thrust to counteract aerodynamic drag and move the rotorcraft in forward flight. Another example of a rotorcraft rotor system is a tail rotor system. A tail rotor system may generate thrust in the same direction as the main rotor system's rotation to counter the torque effect created by the main rotor system.

Rotorcraft may be powered by an engine. Air filters may be provided to prevent unwanted materials from entering the engine.

SUMMARY

Particular embodiments of the present disclosure may provide one or more technical advantages. A technical advantage of one embodiment may include the capability to accurately predict how a degraded engine air filter will perform across a range of engine power levels during operation of the engine air filter. A technical advantage of one embodiment may include the capability to learn performance characteristics of a specific, unique engine. A technical advantage of one embodiment may include the capability to improve vehicle performance, pilot safety, and engine lifespan.

Certain embodiments of the present disclosure may include some, all, or none of the above advantages. One or more other technical advantages may be readily apparent to those skilled in the art from the figures, descriptions, and claims included herein.

BRIEF DESCRIPTION OF THE DRAWINGS

To provide a more complete understanding of the present invention and the features and advantages thereof, reference is made to the following description taken in conjunction with the accompanying drawings, in which:

FIG. 5 shows an example table of delta-pressure values corresponding to the engine power levels and times of the graph of FIG. 4;

FIG. 6 shows an example chart of engine power values and corrected mass flow values contained within the processed engine data of system according to one example embodiment;

FIG. 7 shows an example table of flow values and corresponding engine power values determined using the method of FIG. 3 according to one example embodiment; and FIG. 8 shows a method for determining the current delta-pressure value corresponding to the overall maximum power level for the engine that may be executed at least partially by a system such as the system of FIG. 2 according to one example embodiment.

DETAILED DESCRIPTION OF THE DRAWINGS

Figure 1:
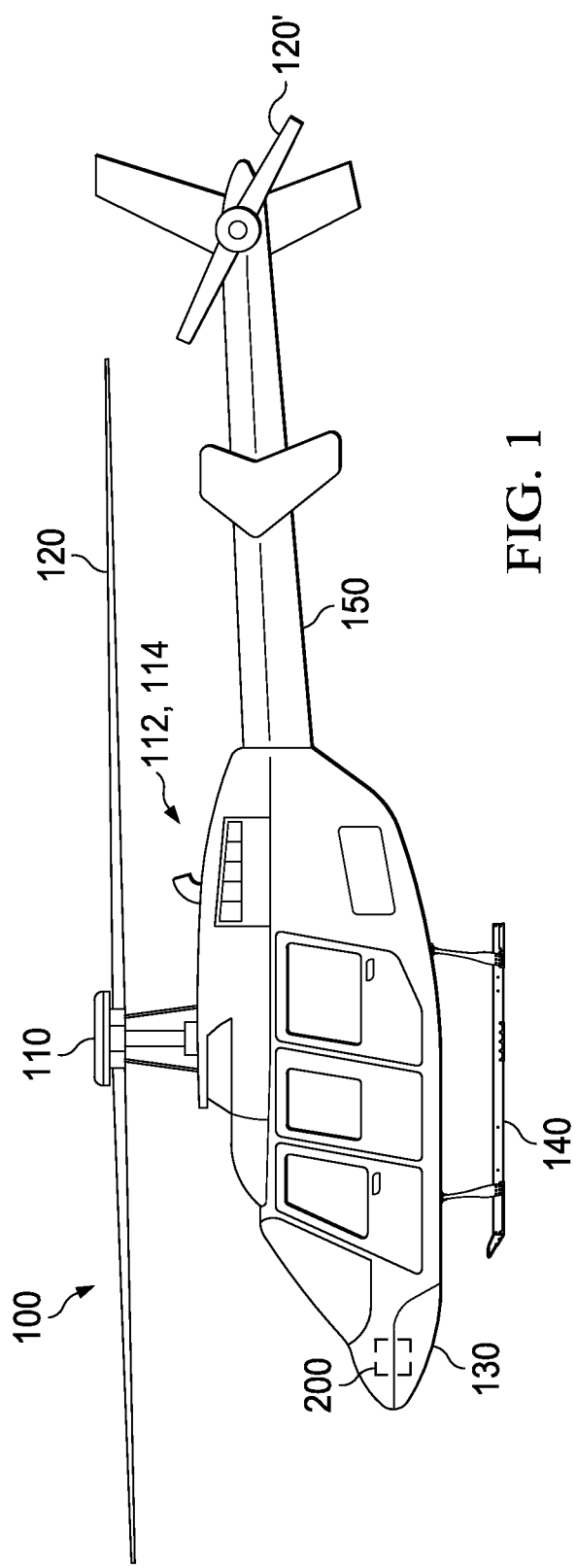
FIG. 1 shows a rotorcraft according to one example embodiment.

FIG. 1 shows a rotorcraft 100 according to one example embodiment. Rotorcraft 100 features a rotor system 110, blades 120, a fuselage 130, a landing gear 140, and an empennage 150. Rotor system 110 may rotate blades 120. Rotor system 110 may include a control system for selectively controlling the pitch of each blade 120 in order to selectively control direction, thrust, and lift of rotorcraft 100. Fuselage 130 represents the body of rotorcraft 100 and may be coupled to rotor system 110 such that rotor system 110 and blades 120 may move fuselage 130 through the air. Landing gear 140 supports rotorcraft 100 when rotorcraft 100 is landing and/or when rotorcraft 100 is at rest on the ground. Empennage 150 represents the tail section of the aircraft and features components of a rotor system 110 and blades 120'. Blades 120' may provide thrust in the same direction as the rotation of blades 120 so as to counter the torque effect created by rotor system 110 and blades 120. Teachings of certain embodiments relating to rotor systems described herein may apply to rotor system 110 and/or other rotor systems, such as other tilt rotor and helicopter rotor systems. It should also be appreciated that teachings regarding rotorcraft 100 may apply to aircraft and vehicles other than rotorcraft, such as airplanes and unmanned aircraft, to name a few examples.

Vehicles such as rotorcraft 100 may be powered by an engine. An air filter may be provided to prevent unwanted materials from entering the engine. In the example of FIG. 1, rotorcraft 100 is equipped with at least one engine 112 and at least one air filter 114.

Over time, the operating condition of the air filter may deteriorate. For example, certain types of air filters may become increasingly clogged such that the air filter allows less and less air through.

Operation of an engine air filter may be expressed by the following formula:

$$\Delta P = K_T Q^2,$$

wherein $\Delta P$ represents the change in pressure across the filter, $K_T$ is a system resistance coefficient, and $Q$ is the volumetric flow. The pressure change, $\Delta P$, may be directly measured using a variety of pressure sensors. In some circumstances, $Q$ may be represented by mass flow if incompressible fluid flow is assumed. The mass flow may be determined based on a relationship between mass flow and engine power, as will be explained in greater detail below.

The system resistance coefficient, $K_T$, may represent the operating condition of the air filter at a particular moment in time. Thus, the value of the system resistance coefficient may change over time because the operating condition of the air filter may change over time. This system resistance coefficient may not, however, change with volumetric flow or engine power; therefore, the resistance coefficient may be presumed fixed at a specific moment in time.

In order for a vehicle such as rotorcraft 100 to operate properly, the air filter should be in sufficient condition so that pressure change across the filter, $\Delta P$, can satisfy certain operating requirements. As seen in the equation above, a change in the system resistance coefficient, $K_T$, over time due to deterioration of the air filter may result in $\Delta P$ no longer satisfying the operating requirements.

The pressure change across the filter, $\Delta P$, also varies as a function volumetric flow, Q. As stated above, the volumetric flow may be a function of engine power. As a result, situations may arise in which $\Delta P$ satisfies operating requirements when engine power is low but then fails to satisfy the operating requirements when engine power increases.

Such a situation may arise, for example, during operation of a vehicle such as rotorcraft 100. Consider rotorcraft 100 flying under normal operating conditions with an air filter that has deteriorated over time. In this scenario, the deteriorated condition of the air filter may not be apparent because the pressure change across the filter, $\Delta P$, satisfies the minimum operating requirements.

But now consider what happens if rotorcraft 100 loses power in one of its two engines. In this situation, known as a one-engine-inoperative (OEI) flight condition, the pilot may increase power in the still-operative second engine to compensate for the loss of power in the first engine. By increasing engine power, however, volumetric flow, Q, also increases. As a result, the pressure change across the filter, $\Delta P$, may no longer satisfy the minimum operating requirements.

Piloting rotorcraft 100 during OEI flight is a poor time to learn that the air filter is clogged and can no longer support minimum operating requirements. When confronted with an OEI flight condition, the pilot may be "task saturated" and be too busy to perform additional actions.

In addition to making a dangerous situation worse for the pilot and crew, failing to predict when the air filter will no longer be able to support minimum operating requirements can result in serious damage to the aircraft. Returning to the OEI example, the pilot may have to bypass the air filter in order to allow enough air into the engine to satisfy operating requirements. Bypassing the air filter, however, may allow an assortment of particulates and debris into the engine, causing serious damage to the engine. In some situations, the damage to the engine may be so significant that the engine must be retired early. This may force the vehicle maintainer to repair or replace a very expensive part (an engine) because a relatively-inexpensive part (a filter) failed.

Thus, the pressure change across the filter, $\Delta P$, should satisfy operating requirements across a range of flow values and engine power values. Accordingly, teachings of certain embodiments recognize the capability to predict what the pressure change across the filter, $\Delta P$, across a range of engine power values based on the current operating condition of the air filter (as expressed by system resistance coefficient, $K_T$). In particular, teachings of certain embodiments recognize the capability to predict what the pressure change across the filter will be if the engine is throttled to maximum power.

The accuracy of such predictions, however, is limited by the accuracy of the input values. In particular, inaccurate values for the volumetric flow variable, Q, may result in inaccurate assessments of air filter health.

As stated above, a relationship may exist between volumetric flow, Q, and engine power. An engine manufacturer may provide estimates of this relationship based on their testing data. These estimates, however, may not be sufficiently accurate, especially at low engine power. In particular, estimates for how a model of engine will perform may not account for the uniqueness of each particular engine and the uniqueness of the operating environment of each particular engine (e.g., what vehicle the particular engine is installed in and where that vehicle operates).

Accordingly, teachings of certain embodiments recognize the capability to collect volumetric flow data unique to a particular engine and then use this unique data to assess the condition of an air filter associated with that particular engine. In this manner, a measurement system may "learn" how an engine operates and then measure air filter health based on this learned information. Teachings of certain embodiments recognize that utilizing learned engine data may result in more accurate predictions regarding how an associated air filter will perform across a range of engine power settings, including a maximum engine power setting.

Figure 2:
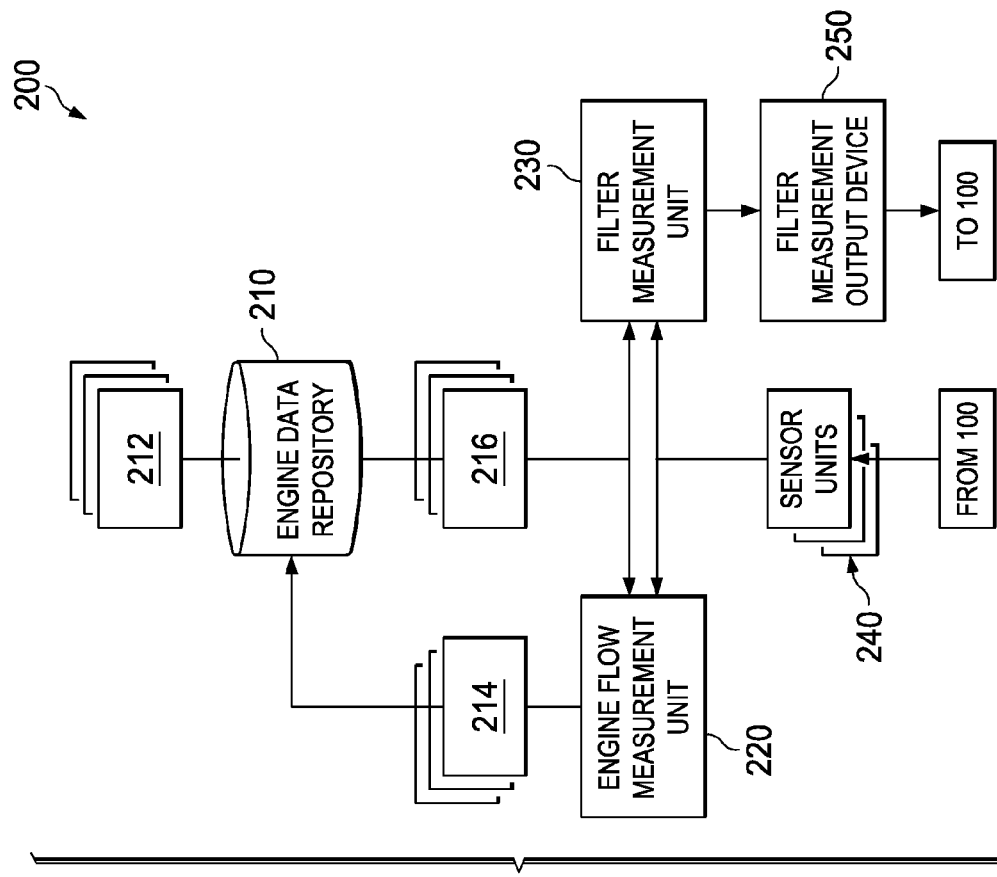
FIG. 2 shows a measurement system that may be installed on or communicate with a vehicle such as the rotorcraft of FIG. 1 according to one example embodiment.
Figure 2:
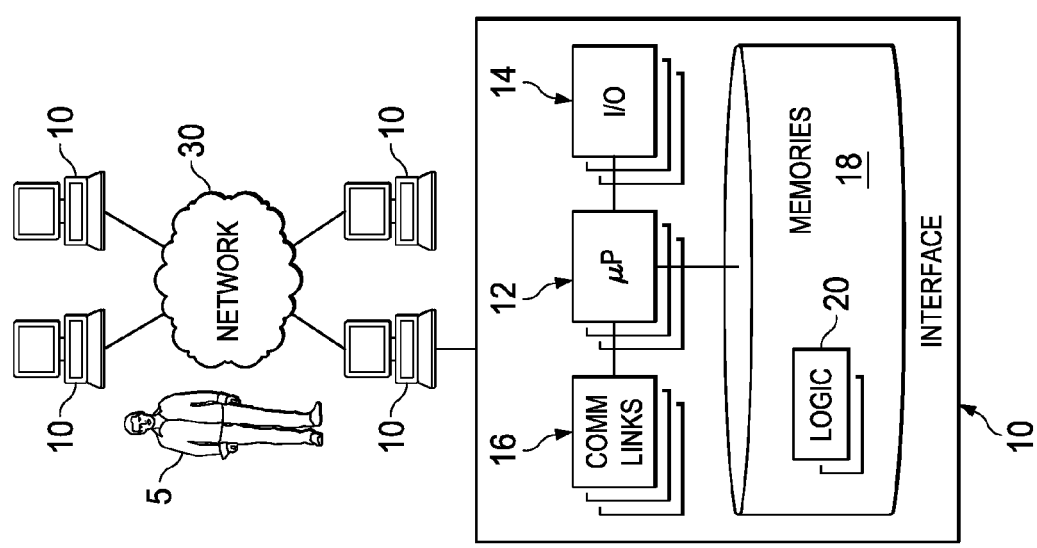

FIG. 2 shows a health and maintenance system 200 according to one example embodiment. In the example of FIG. 2, system 200 features an engine data repository 210, an engine flow measurement unit 220, a filter measurement unit 230, sensor units 240, and a filter measurement output device 250, which may be implemented by one or more computers 10 communicating across one or more networks 30 and accessible by a user 5. Example of computer systems 10 may include, but are not limited to, a computer installed on-board an aircraft such as rotorcraft 100 (e.g., a flight control computer), a ground station computer, a maintenance computer, a data processing server, and an end-user computer. In various embodiments, elements of system 200 may be installed on-board an aircraft, off-board, or a combination of the two.

Users 5 may access system 200 through computer systems 10. Users 5 may include any individual, group of individuals, entity, machine, and/or mechanism that interacts with computer systems 10. Examples of users 5 include, but are not limited to, a maintenance person, pilot, engineer, technician, owner, operator, contractor, agent, and/or employee. Some of these terms may be used interchangeably throughout; for example, an owner may also be an operator. Generally, these terms should be construed to represent any party having a role associated with a vehicle such as rotorcraft 100 without the role being given a specific or narrow meaning.

Users 5 may be associated with an organization. An organization may include any social arrangement that pursues collective goals. One example of an organization is a business. A business is an organization designed to provide goods or services, or both, to consumers, governmental entities, and/or other businesses.

Computer system 10 may include processors 12, input/output devices 14, communications links 16, and memory 18. In other embodiments, computer system 10 may include more, less, or other components. Computer system may be operable to perform one or more operations of various embodiments. Although the embodiment shown provides one example of computer system 10 that may be used with other embodiments, such other embodiments may utilize computers other than computer system 10. Additionally, embodiments may also employ multiple computer systems 10 or other computers networked together in one or more public and/or private computer networks, such as one or more networks 30.

Processors 12 represent devices operable to execute logic contained within a medium. Examples of processor 12 include one or more microprocessors, one or more applications, and/or other logic. Computer system 10 may include one or multiple processors 12.

Input/output devices 14 may include any device or interface operable to enable communication between computer system 10 and external components, including communication with a user or another system. Example input/output devices 14 may include, but are not limited to, a mouse, keyboard, display, and printer.

Network interfaces 16 are operable to facilitate communication between computer system 10 and another element of a network, such as other computer systems 10. Network interfaces 16 may connect to any number and combination of wireline and/or wireless networks suitable for data transmission, including transmission of communications. Network interfaces 16 may, for example, communicate audio and/or video signals, messages, internet protocol packets, frame relay frames, asynchronous transfer mode cells, and/or other suitable data between network addresses. Network interfaces 16 connect to a computer network or a variety of other communicative platforms including, but not limited to, a public switched telephone network (PSTN); a public or private data network; one or more intranets; a local area network (LAN); a metropolitan area network (MAN); a wide area network (WAN); a wireline or wireless network; a local, regional, or global communication network; an optical network; a satellite network; a cellular network; an enterprise intranet; all or a portion of the Internet; other suitable network interfaces; or any combination of the preceding.

Memory 18 represents any suitable storage mechanism and may store any data for use by computer system 10. Memory 18 may comprise one or more tangible, computer-readable, and/or computer-executable storage medium. Examples of memory 18 include computer memory (for example, Random Access Memory (RAM) or Read Only Memory (ROM)), mass storage media (for example, a hard disk), removable storage media (for example, a Compact Disk (CD) or a Digital Video Disk (DVD)), database and/or network storage (for example, a server), and/or other computer-readable medium.

In some embodiments, memory 18 stores logic 20. Logic 20 facilitates operation of computer system 10. Logic 20 may include hardware, software, and/or other logic. Logic 20 may be encoded in one or more tangible, non-transitory media and may perform operations when executed by a computer. Logic 20 may include a computer program, software, computer executable instructions, and/or instructions capable of being executed by computer system 10. Example logic 20 may include any of the well-known OS2, UNIX, Mac-OS, Linux, and Windows Operating Systems or other operating systems. In particular embodiments, the operations of the embodiments may be performed by one or more computer readable media storing, embodied with, and/or encoded with a computer program and/or having a stored and/or an encoded computer program. Logic 20 may also be embedded within any other suitable medium without departing from the scope of the invention.

Various communications between computers 10 or components of computers 10 may occur across a network, such as network 30. Network 30 may represent any number and combination of wireline and/or wireless networks suitable for data transmission. Network 30 may, for example, communicate internet protocol packets, frame relay frames, asynchronous transfer mode cells, and/or other suitable data between network addresses. Network 30 may include a public or private data network; one or more intranets; a local area network (LAN); a metropolitan area network (MAN); a wide area network (WAN); a wireline or wireless network; a local, regional, or global communication network; an optical network; a satellite network; a cellular network; an enterprise intranet; all or a portion of the Internet; other suitable communication links; or any combination of the preceding. Although the illustrated embodiment shows one network 30, teachings of certain embodiments recognize that more or fewer networks may be used and that not all elements may communicate via a network. Teachings of certain embodiments also recognize that communications over a network is one example of a mechanism for communicating between parties, and any suitable mechanism may be used.

In the example of FIG. 2, engine data repository 210 stores performance information associated with a particular engine. In the example embodiment of FIG. 2, engine data repository 210 receives baseline engine data 212 from an outside source, such as from an engine manufacturer. This baseline engine data 212 may not be unique to a particular engine, but rather may be generic to a category of engines, such as a model of engines.

Engine data repository 210 may also store engine data that is unique to a particular engine. In the example of FIG. 2, engine data repository 210 receives engine data updates 214 from engine flow measurement unit 220. These engine data updates 214 may be unique to a particular engine.

Engine data repository 210 may also store and provide processed engine data 216. Processed engine data 216 may be based on the baseline engine data 212 and/or the engine data updates 214 received by engine data repository 210. For example, in one embodiment, processed engine data 216 may represent the combination of baseline engine data 212 and engine data updates 214. In another example embodiment, processed engine data 216 includes all or some of engine data updates 214 but does not include all of the baseline engine data 212 because engine data updates 214 are presumed to be more accurate than baseline engine data 212 over certain data ranges.

Baseline engine data 212, engine data updates 214, and processed engine data 216 may represent a variety of different categories of data. In one example embodiment, baseline engine data 212, engine data updates 214, and processed engine data 216 includes engine power values and associated flow values (e.g., volumetric flow values or mass flow values). Engine power values may include any representation of engine power. In some example embodiments, engine power values may be expressed by a value such as revolutions-per-minute (rpms), which may have a relationship with engine power. In other embodiments, a metric other than rpms (such as engine torque) may be used. Although example embodiments described herein may appear to use terms such as "engine power" and "rpms" interchangeably, metrics other than rpms may be used when appropriate. Likewise, references to engine power may also include references to other metrics that are analogous or somehow related to engine power.

Engine flow measurement unit 220 measures engine flow unique to a particular engine and generates engine data updates 214. In the example of FIG. 2, engine flow measurement unit 220 receives processed engine data 216 and input from sensor units 240 and generates engine data updates 214. In some embodiments, engine data repository 210 and engine flow measurement unit 220 may operate in a continuously-iterative manner. For example, engine flow measurement unit 220 may receive processed engine data 216 and generate engine data updates 214; engine data repository 210 may add the engine data updates 214 to existing engine data to yield new processed engine data 216, which engine flow measurement unit 220 may utilize to generate new engine data updates 214, and so forth.

In some embodiments, engine flow measurement unit 220 may utilize baseline engine data 212 instead of processed engine data 216. Such may be the case, for example, if no processed engine data 216 exists yet. In this example, engine flow measurement unit 220 may start this iterative process using baseline engine data 212 and then may switch to using processed engine data 216 at a later time.

Filter measurement unit 230 measures aspects associated with the air filter, such as the air filter operating condition or the change in pressure across the air filter at different engine operating conditions. Filter measurement output device 250 receives measurements from filter measurement unit 230 and provides some sort of output. Examples of such an output may include, but are not limited to, an alert to the pilot that the air filter condition may be degraded or an alert to the maintenance crew that the air filter should be repaired or replaced.

Filter measurement unit 230 utilizes processed engine data 216 to measure aspects associated with the air filter. Teachings of certain embodiments recognize that using processed engine data 216 may lead to more accurate air filter measurements than using baseline engine data 212.

In the example of FIG. 2, engine flow measurement unit 220 and filter measurement unit 230 may perform various calculations using information from sensor units 240. Sensor units 240 may represent any device capable of collecting information from a vehicle such as rotorcraft 100. Examples of sensor units 240 may include sensors installed onboard the vehicle or devices in communication with sensors installed onboard the vehicle. Examples of information collected from the vehicle may include, but are not limited to, performance data such as delta-pressure values (ΔP) and associated engine power values (rpms).

Figure 3:
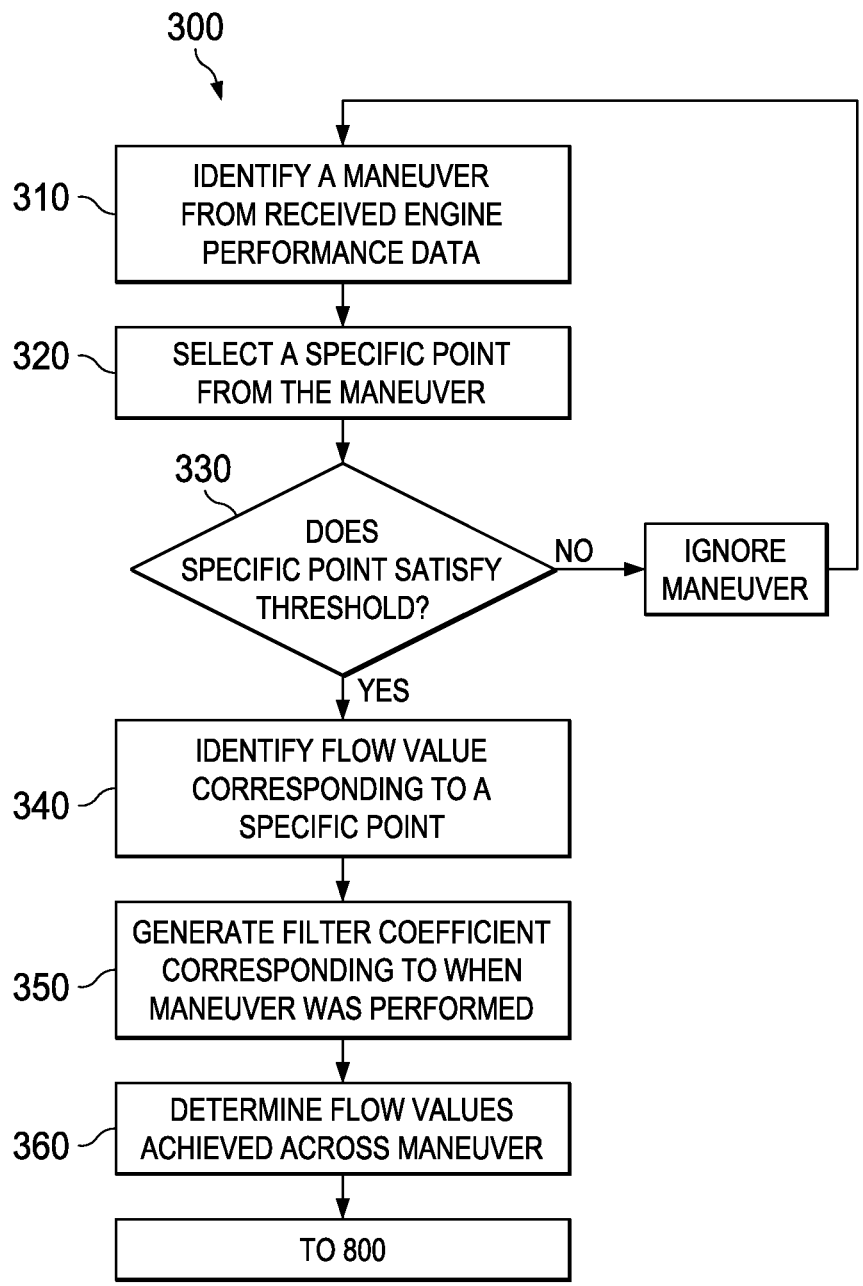
FIG. 3 shows a method for measuring flow values across a range of engine power values that may be executed at least partially by a system such as the system of FIG. 2 according to one example embodiment.

FIG. 3 shows a method 300 for measuring flow values across a range of engine power values according to one example embodiment. In some embodiments, all or some of the steps of method 300 may be performed by the engine flow measurement unit 220 of system 200. References are made to FIGS. 4-7, which illustrate various concepts utilized during the performance of method 300.

At step 310 of method 300, a maneuver is identified from received engine performance data. Examples of the received engine performance data may include, but are not limited to, performance data such as delta-pressure values (ΔP) and associated engine power values (rpms).

Figure 4:
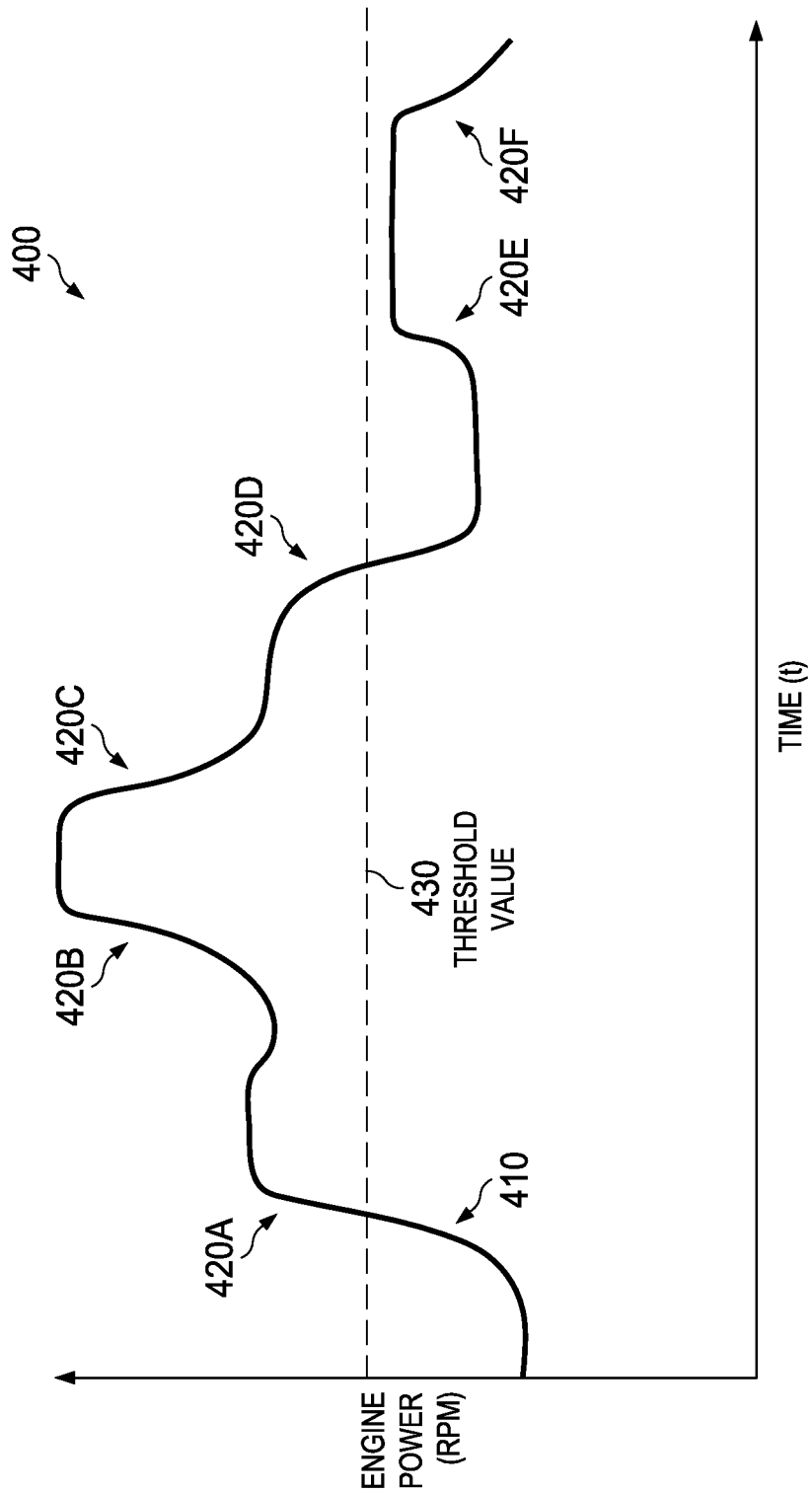
FIG. 4 shows an example graph charting two types of received engine performance data: engine power (rpm) over time (t)

FIG. 4 shows an example graph 400 that charts a type of received engine performance data, i.e., engine power (rpm) over time (t). In this example, each received engine power value may also have a corresponding delta-pressure value (ΔP), such as shown in the example table 500 of FIG. 5. In table 500, each point in time (n) has a corresponding engine power level ($RPM_n$) and delta-pressure value ($\Delta P_n$).

In the example graph 400 of FIG. 4, an engine power history 410 is charted over time. In this example, maneuvers may be identified from engine power history 410. For example, in FIG. 4, six "power sweeps" 420a-420f are identified. In this example, a power sweep may represent a significant change in engine power over a small period of time.

At step 320 of method 300, a specific point is selected from the identified maneuver. One example of selecting a specific point may include selecting a specific engine power value and corresponding specific delta-pressure value from the identified maneuver. Returning to the example of FIG. 4, selecting a specific point from an identified maneuver may include selecting the highest engine power value from an identified power sweep, such as power sweeps 420a-420f. Teachings of certain embodiments recognize that some engine data (such as data provided by engine manufacturers) may be more accurate at higher engine power levels, so selecting the highest engine power value from an identified power sweep at step 320 may lead to more accurate results. In the example table 500 of FIG. 5, the maximum engine power value is expressed as $RPM_{MAX\_M}$ and the corresponding delta-pressure value is expressed as $\Delta P_{MAX\_M}$.

Not only may engine data (such as data provided by engine manufacturers) be more accurate at higher engine power levels, but there may a threshold above which engine power values are presumed accurate but below which engine power values are not presumed accurate. In the example of FIG. 4, an example threshold engine value is shown as threshold value 430.

At step 330 of method 300, the selected specific point is compared to a threshold value, such as a threshold engine power level value. If the selected specific point satisfies the threshold value, then the method proceeds to step 340; if not, the identified maneuver may be disregarded, and a new maneuver may be identified.

Returning to the example of FIG. 4, the selected point may satisfy the threshold value if, for example, the highest engine power value in a power sweep ($RPM_{MAX\_M}$) is higher than threshold engine power value 430. In the example of FIG. 3, four power sweeps (420a, 420b, 420c, and 420d) satisfy the threshold, but two power sweeps (420e and 420f) do not have engine power values high enough to satisfy the threshold.

At step 340 of method 300, a flow value (Q) is identified corresponding to the specific point. In one example embodiment, the identified flow value (Q) is the corresponding to $RPM_{MAX\_M}$. The value of $Q_{MAX\_M}$ $Q_{MAX\_M}$ corresponding to $RPM_{MAX\_M}$ may be identified from processed engine data 216.

FIG. 6 shows an example chart 600 of engine power values and corrected mass flow values contained within processed engine data 216 according to one example embodiment. In the example of FIG. 6, processed engine data 216 represents only baseline engine data 212, which may be the case, for example, if the only information available is information provided by the engine manufacturer. In the example of FIG. 6, the maximum power level obtained during the power sweep ($RPM_{MAX\_M}$) is located somewhere above threshold value 430 and below the overall maximum power level for the engine, $RPM_{MAX}$.

At step 350 of method 300, the filter coefficient is generated corresponding to when the maneuver was performed. Returning to the previous example, the filter coefficient for the power sweep may be expressed in the following formula:

$$\Delta P_{MAX\_M} = K_{T_M}(Q_{MAX\_M})^2,$$

wherein $\Delta P_{MAX\_M}$ represents the change in pressure across the filter, $K_{T_M}$ is the filter coefficient for the power sweep, and $Q_{MAX\_M}$ is the flow determined at step 340. In this example, $\Delta P_{MAX\_M}$ may be determined by identifying the delta-pressure value collected by sensor units 240 corresponding to the time when the maximum power level for the power sweep ($RPM_{MAX\_M}$) was achieved.

At step 360 of method 300, the flow values achieved over the course of the maneuver are determined. As explained above, the system resistance coefficient may change over time due to degradations in air filter quality but may not necessarily change due to differences in air flow volume. Accordingly, teachings of certain embodiments recognize the capability to use the power sweep filter coefficient, $K_{T_M}$, to solve for the flow values (Q) achieved across the entire power sweep. These flow values (Q) achieved across the entire power sweep may be expressed in the following formula:

$$\Delta P_n = K_{T_M}(Q_n)^2.$$

In this example, each $\Delta P_n$ may be determined by identifying the delta-pressure value collected by sensor units 240 at time n during the power sweep.

If the values for $Q_n$ are known for each point in time n in a power sweep, then these flow values for $Q_n$ may be correlated back to the engine power values $RPM_n$ achieved during the power sweep, as shown in FIG. 5.

FIG. 7 shows an example table 700 of flow values $Q_n$ and corresponding engine power values $RPM_n$. In one example embodiment, table 700 may represent an example of engine data updates 214 that may be provided to engine data repository 210 and incorporated into processed engine data 216. Teachings of certain embodiments recognize that the flow values $Q_n$ obtained through system 200 may be more accurate than the baseline engine data 212 provided by the engine manufacturer, especially for engine power values below threshold value 430.

Using accurate flow values, the current delta-pressure value corresponding to the overall maximum power level for the engine, $RPM_{MAX}$, may be determined. For example, FIGURE shows a method 800 for determining the current delta-pressure value corresponding to the overall maximum power level for the engine according to one example embodiment. In some embodiments, all or some of the steps of method 800 may be performed by the filter measurement unit 230 of system 200.

As stated above, the system coefficient may change over time due to degradation in the operating condition of the air filter. Accordingly, in order to determine the current delta-pressure value corresponding to the overall maximum power level for the engine, the current system coefficient is determined at step 810. The current filter coefficient, $K_{TC}$, may be expressed in the following formula:

$$\Delta P_C = K_{TC}(Q_C)^2.$$

In this example, $\Delta P_C$ may represent the current delta-pressure value provided by sensor units 240, and $Q_C$ may be determined by identifying the flow value in processed engine data 216 corresponding to the current engine power level identified by sensor units 240.

At step 820, the overall maximum power value for the engine, $RPM_{MAX}$, may be determined. In some scenarios, the overall maximum power value for the engine may be provided by the engine manufacturer, as seen in the example graph 600 of FIG. 6. Once the overall maximum power value for the engine, $RPM_{MAX}$, is known, the corresponding maximum flow value, $Q_{MAX}$, may be determined from processed engine data 216.

At step 830, the current maximum delta-pressure value for the air filter may be determined. This current maximum delta-pressure value may be expressed by the following formula:

$$\Delta P_{MAX\_c} = K_{T_c}(Q_{MAX})^2$$

This current maximum delta-pressure value may represent, among other things, what the delta-pressure value would be if the engine power was increased the maximum engine power level.

Although this example focuses on the maximum delta-pressure value, teachings of certain embodiments recognize the capability to predict the delta-pressure value across a range of engine power levels, flow volumes, and air filter conditions.

Teachings of certain embodiments recognize that methods such as methods 300 and 800 may be performed during operation of a vehicle such as rotorcraft 100. For example, method 300 may continuously identify new maneuvers and add new engine data to the repository. In this example, method 800 may continuously monitor the operating condition of the air filter as both the air filter status and the engine data change over time. In this example, engine flow measurement unit 220 may continuously "learn" how the engine operates, which may result in the delta-pressure predictions provided by filter measurement unit 230 becoming more accurate over time.

Modifications, additions, or omissions may be made to the systems and apparatuses described herein without departing from the scope of the invention. The components of the systems and apparatuses may be integrated or separated. Moreover, the operations of the systems and apparatuses may be performed by more, fewer, or other components. The methods may include more, fewer, or other steps. Additionally, steps may be performed in any suitable order.

Although several embodiments have been illustrated and described in detail, it will be recognized that substitutions and alterations are possible without departing from the spirit and scope of the present invention, as defined by the appended claims.

To aid the Patent Office, and any readers of any patent issued on this application in interpreting the claims appended hereto, applicants wish to note that they do not intend any of the appended claims to invoke paragraph 6 of 35 U.S.C. § 112 as it exists on the date of filing hereof unless the words "means for" or "step for" are explicitly used in the particular claim.

What is claimed is:

1. An engine flow measurement device, comprising:
   an engine data repository configured to store an engine data set comprising a plurality of stored flow values and a plurality of stored engine power values corresponding to the plurality of stored flow values;
   one or more sensor units configured to receive, during operation of an aircraft, performance data associated with performance of an engine having an associated air filter, the performance data comprising a plurality of delta-pressure values and a plurality of engine power values corresponding to the delta-pressure values, each delta-pressure value representing a difference in pressure between the inlet and the exhaust of the air filter;
   a measurement unit configured to:
      identify, from the performance data, a power sweep performed during operation of the aircraft;
      measure, for the identified power sweep, a plurality of power sweep flow values achieved during performance of the power sweep, the plurality of power sweep flow values corresponding to a plurality of power sweep engine power values, each of the plurality of power sweep flow values representing a volume of air flow through the air filter at a particular moment during performance of the power sweep; and transmit the plurality of power sweep flow values to the engine data repository.

2. The engine flow measurement device of claim 1, the measurement unit comprising a processor configured to measure the plurality of power sweep flow values and to store the plurality of power sweep flow values in one or more memory locations associated with the engine data repository.

3. The engine flow measurement device of claim 1, the measurement unit further configured to store the plurality of power sweep flow values with the engine data set in the engine data repository.

4. The engine flow measurement device of claim 1, wherein measuring the plurality of power sweep flow values comprises:

determining, from the performance data based on the identified power sweep, a plurality of power sweep delta-pressure values and a plurality of power sweep engine power values, the plurality of power sweep delta-pressure values being a subset of the plurality of delta-pressure values and the plurality of power sweep engine power values being a subset of the plurality of engine power values;

identifying a specific delta-pressure value and a corresponding specific engine power value from the plurality of power sweep delta-pressure values and the plurality of power sweep engine power values;

identifying, from the engine data set, a specific flow value corresponding to the specific engine power value;

generating a filter coefficient corresponding to a time when the power sweep was performed, the filter coefficient being a function of the specific flow value from the engine data set and the specific delta-pressure value from the performance data; and determining the plurality of power sweep flow values achieved during performance of the power sweep as a function of the generated filter coefficient and the plurality of power sweep delta-pressure values.

5. The engine flow measurement device of claim 4, the measurement unit further configured to determine whether the specific engine power value is higher than a predetermined acceptable threshold value and identify the specific flow value only if the specific engine power value is higher than the predetermined acceptable threshold value.

6. The engine flow measurement device of claim 4, wherein identifying the specific delta-pressure value and the corresponding specific engine power value from the plurality of power sweep delta-pressure values and the plurality of power sweep engine power values comprises selecting the highest of the engine power values from the plurality of power sweep engine power values and identifying the delta-pressure value corresponding to the highest of the engine power values from the plurality of power sweep engine power values.

7. The engine flow measurement device of claim 1, wherein the plurality of stored engine power values comprises power values generic to a category of engines.

8. The engine flow measurement device of claim 1, wherein the plurality of stored engine power values comprises a first plurality of power values generic to a category of engines and a second plurality of power values specific to an individual engine.

9. A method of measuring air flow through an engine during operation of an aircraft, comprising:

storing, in an engine data repository, an engine data set comprising a plurality of stored flow values and a plurality of stored engine power values corresponding to the plurality of stored flow values;

receiving, during operation of an aircraft, performance data associated with performance of an engine having an associated air filter, the performance data comprising a plurality of delta-pressure values and a plurality of engine power values corresponding to the delta-pressure values, each delta-pressure value representing a difference in pressure between the inlet and the exhaust of the air filter;

identifying, from the performance data, a power sweep performed during operation of the aircraft;

measuring, for the identified power sweep, a plurality of power sweep flow values achieved during performance of the power sweep, the plurality of power sweep flow values corresponding to a plurality of power sweep engine power values, each of the plurality of power sweep flow values representing a volume of air flow through the air filter at a particular moment during performance of the power sweep; and transmitting the plurality of power sweep flow values to the engine data repository.

10. The method of claim 9, further comprising storing the plurality of power sweep flow values in one or more memory locations associated with the engine data repository.

11. The method of claim 9, wherein measuring the plurality of power sweep flow values comprises:

determining, from the performance data based on the identified power sweep, a plurality of power sweep delta-pressure values and a plurality of power sweep engine power values, the plurality of power sweep delta-pressure values being a subset of the plurality of delta-pressure values and the plurality of power sweep engine power values being a subset of the plurality of engine power values;

identifying a specific delta-pressure value and a corresponding specific engine power value from the plurality of power sweep delta-pressure values and the plurality of power sweep engine power values;

identifying, from the engine data set, a specific flow value corresponding to the specific engine power value;

generating a filter coefficient corresponding to a time when the power sweep was performed, the filter coefficient being a function of the specific flow value from the engine data set and the specific delta-pressure value from the performance data; and determining the plurality of power sweep flow values achieved during performance of the power sweep as a function of the generated filter coefficient and the plurality of power sweep delta-pressure values.

12. The method of claim 11, further comprising determining whether the specific engine power value is higher than a predetermined acceptable threshold value and identify the specific flow value only if the specific engine power value is higher than the predetermined acceptable threshold value.

13. The method of claim 11, wherein identifying the specific delta-pressure value and the corresponding specific engine power value from the plurality of power sweep delta-pressure values and the plurality of power sweep engine power values comprises selecting the highest of the engine power values from the plurality of power sweep engine power values and identifying the delta-pressure value corresponding to the highest of the engine power values from the plurality of power sweep engine power values.

14. The method of claim 9, wherein the plurality of stored engine power values comprises power values generic to a category of engines.

15. The method of claim 9, wherein the plurality of stored engine power values comprises a first plurality of power values generic to a category of engines and a second plurality of power values specific to an individual engine.

16. A rotorcraft, comprising:
a body;
a power train coupled to the body and comprising one or more power sources, a drive shaft coupled to the one or more power sources, and an air filter associated with the one or more power sources;
a rotor system coupled to the power train and comprising a plurality of rotor blades; and
an engine flow measurement device at least partially disposed within the body, the engine flow measurement device comprising:
an engine data repository configured to store an engine data set comprising a plurality of stored flow values and a plurality of stored engine power values corresponding to the plurality of stored flow values;
one or more sensor units associated with the power train and configured to receive, during operation of the rotorcraft, performance data associated with performance of an engine having an associated air filter, the performance data comprising a plurality of delta-pressure values and a plurality of engine power values corresponding to the delta-pressure values, each delta-pressure value representing a difference in pressure between the inlet and the exhaust of the air filter; and
a measurement unit configured to identify, from the performance data, a power sweep performed during operation of the aircraft and to measure, for the identified power sweep, a plurality of power sweep flow values achieved during performance of the power sweep, the plurality of power sweep flow values corresponding to a plurality of power sweep engine power values, each of the plurality of power sweep flow values representing a volume of air flow through the air filter at a particular moment during performance of the power sweep, the measurement unit further configured to transmit the plurality of power sweep flow values to the engine data repository.

17. The rotorcraft of claim 16, the measurement unit comprising a processor configured to measure the plurality of power sweep flow values and to store the plurality of power sweep flow values in one or more memory locations associated with the engine data repository.

18. The rotorcraft of claim 16, wherein measuring the plurality of power sweep flow values comprises:
determining, from the performance data based on the identified power sweep, a plurality of power sweep delta-pressure values and a plurality of power sweep engine power values, the plurality of power sweep delta-pressure values being a subset of the plurality of delta-pressure values and the plurality of power sweep engine power values being a subset of the plurality of engine power values;
identifying a specific delta-pressure value and a corresponding specific engine power value from the plurality of power sweep delta-pressure values and the plurality of power sweep engine power values;
identifying, from the engine data set, a specific flow value corresponding to the specific engine power value;
generating a filter coefficient corresponding to a time when the power sweep was performed, the filter coefficient being a function of the specific flow value from the engine data set and the specific delta-pressure value from the performance data; and
determining the plurality of power sweep flow values achieved during performance of the power sweep as a function of the generated filter coefficient and the plurality of power sweep delta-pressure values.

19. The rotorcraft of claim 18, the measurement unit further configured to determine whether the specific engine power value is higher than a predetermined acceptable threshold value and identify the specific flow value only if the specific engine power value is higher than the predetermined acceptable threshold value.

20. The rotorcraft of claim 18, wherein identifying the specific delta-pressure value and the corresponding specific engine power value from the plurality of power sweep delta-pressure values and the plurality of power sweep engine power values comprises selecting the highest of the engine power values from the plurality of power sweep engine power values and identifying the delta-pressure value corresponding to the highest of the engine power values from the plurality of power sweep engine power values.

* * * * *